US006730509B2

(12) United States Patent
VanErdewyk

(10) Patent No.: US 6,730,509 B2
(45) Date of Patent: May 4, 2004

(54) CONTROLLED RELEASE DISPENSER

(75) Inventor: Michael Z. VanErdewyk, Lakeville, MN (US)

(73) Assignee: Bioverse, Inc., Bloomington, MN (US)

( * ) Notice: Subject to any disclaimer, the term of this patent is extended or adjusted under 35 U.S.C. 154(b) by 94 days.

(21) Appl. No.: 09/764,175

(22) Filed: Jan. 17, 2001

(65) Prior Publication Data

US 2002/0160506 A1 Oct. 31, 2002

(51) Int. Cl.$^7$ .................................................. C12M 1/26

(52) U.S. Cl. ................. 435/262; 435/297.1; 435/304.1; 435/307.1; 435/309.1; 210/198.1; 422/265

(58) Field of Search ................................ 435/243, 245, 435/262, 262.5, 297.1, 297.2, 289.1, 307.1, 299.1, 299.2, 304.1, 304.2, 309.1, 264; 422/265; 210/606, 608, 610, 615–617, 150, 198.1

(56) References Cited

U.S. PATENT DOCUMENTS 4,613,330 A * 9/1986 Michelson .................. 424/424
4,630,634 A * 12/1986 Sasaki et al. ............... 137/268
4,670,149 A * 6/1987 Francis ........................ 210/150
4,810,385 A * 3/1989 Hater et al. ................. 210/150
5,022,182 A * 6/1991 Anderson ................... 47/48.5
5,770,079 A * 6/1998 Haase ......................... 210/150
5,879,932 A * 3/1999 Van Erdewyk et al. .. 210/198.1
5,972,332 A * 10/1999 Rees et al. .................. 424/422

FOREIGN PATENT DOCUMENTS

GB 2124864 A * 2/1984 ............ A01K/7/02

* cited by examiner

*Primary Examiner*—William H. Beisner
(74) *Attorney, Agent, or Firm*—Haugen Law Firm PLLP

(57) ABSTRACT

A porous container for controllably releasing various substances into surrounding fluid environments includes a porous material having pores sized and configured to allow the substances contained within the container to pass through the pores at a rate of no more than about 0.5 g/day/cm$^2$. In a particular embodiment, the porous container is adapted to controllably release microorganisms into surrounding fluid environments, which microorganisms may be cultured within the porous container. The porous container may also be utilized with a variety of dispensing vessels to obtain desired controlled release characteristics.

16 Claims, 1 Drawing Sheet

CONTROLLED RELEASE DISPENSER

FIELD OF THE INVENTION

The present invention relates to controlled release of various substances into fluid environments generally, and more particularly to a device providing a controlled release of various substances including microorganisms into aqueous environments. This invention also relates to methods for controllably releasing various substances from a contained source.

BACKGROUND OF THE INVENTION

A number of applications exist today in which various materials are desired to be dispensed into fluid environments, particularly into aqueous environments. Further, many such applications seek a controlled release function to slowly release such materials over a desired period of time. Such applications include, for example, chemical additions to drinking water, swimming pools, water fountains, and waste water treatment facilities, preservation materials into fluid supply stocks, and additives to various food and beverage preparation mixes. A variety of other applications for releasing materials into desired fluids exist today.

One problem that exists in implementing such applications is the difficulty in controllably dispensing such materials at a desired rate. Many instances arise in which a slow, controlled release is preferable over an instantaneous "charge" to the fluid. As a particular example of a situation where controlled release is desirable is the release of microorganisms into contaminated water, as described in U.S. Pat. No. 5,879,932, assigned to the assignee in the present application. Thus, a reliable technique for controllably releasing various substances into surrounding fluid environments in a variety of fluid flow conditions is desired.

Accordingly, it is a principle object of the present invention to provide a device for controllably releasing substances into fluid environments.

It is a further object of the present invention to provide a device for controllably releasing substances into flowing fluid environments.

It is a still further object of the present invention to provide a biodegradable device for controllably releasing substances into fluid environments.

It is a still further object of the present invention to provide a device for controllably releasing microorganisms into aqueous fluid environments.

It is a yet further object of the present invention to provide a device for culturing and controllably releasing microorganisms into fluid environments.

It is another object of the present invention to controllably release substances into fluid environments at a rate of no more than 0.5 g/day/$cm^2$.

It is a still further object of the present invention to provide a means for floating a controlled release device near the top surface of the fluid receiving the dispensed substances.

It is a yet further object of the present invention to provide a means for sinking a controlled release device to the bottom of the fluid receiving the released substances.

SUMMARY OF THE INVENTION

By means of the present invention, substances may be controllably released into surrounding fluid environments at a rate of no more than 0.5 g/day/$cm^2$ through the utilization S of a porous container. Such controlled release is achieved by placing the substances to be released within the porous container and subsequently placing the charged container into the desired fluid.

One embodiment of the present invention provides for a sealed pouch comprising porous material having pores sized and configured to allow the substances contained within the pouch to pass through the pores at a rate of no more than about 0.5 g/day/$cm^2$. The sealed pouch may be biodegradable, and is preferably fabricated from a fibrous paper material.

Another preferred embodiment of the present invention includes a porous container for controllably releasing microorganisms contained therein into fluid environments. In such an embodiment, the porous container preferably initially contains a mixture of microorganisms, nutrients, and a suspending fluid. As in other embodiments, the porous container may be biodegradable, and is preferably fabricated from a fibrous paper material.

Another embodiment of the present invention includes a dispensing vessel and a porous container disposed within the dispensing vessel, wherein the porous container comprises porous material having pores which are sized and configured to allow substances to pass through the pores at a controlled rate. Preferably, at least a portion of the dispensing vessel includes open channels extending through an exterior of the vessel, such that fluids surrounding the dispensing vessel may be in contact with the porous container disposed therein. In particularly preferred embodiments, the dispensing vessel includes a floating portion and a growth chamber that is removably secured to the floating portion, with the growth chamber depending downwardly therefrom. The hollow chamber defined within the growth chamber is preferably open to the surrounding fluid such that the porous container being disposed in the hollow chamber may be in fluid communication with the fluid surrounding the growth chamber.

The present invention also contemplates a method for culturing and controllably releasing microorganisms into fluid environments. The method includes providing a porous container having microorganisms, nutrients, and a suspension fluid disposed therein, with the porous container comprising material having pores which are sized and configured to allow the microorganisms to pass through the pores at a rate of no more than about 0.5 g/day/$cm^2$. The porous container is then placed into an aqueous environment, thereby allowing the microorganisms to culture within the container and to controllably release into the aqueous environment.

BRIEF DESCRIPTION OF THE INVENTION

DETAILED DESCRIPTION OF THE PREFERRED EMBODIMENTS

The object and advantages numerated above together with other objects, features and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
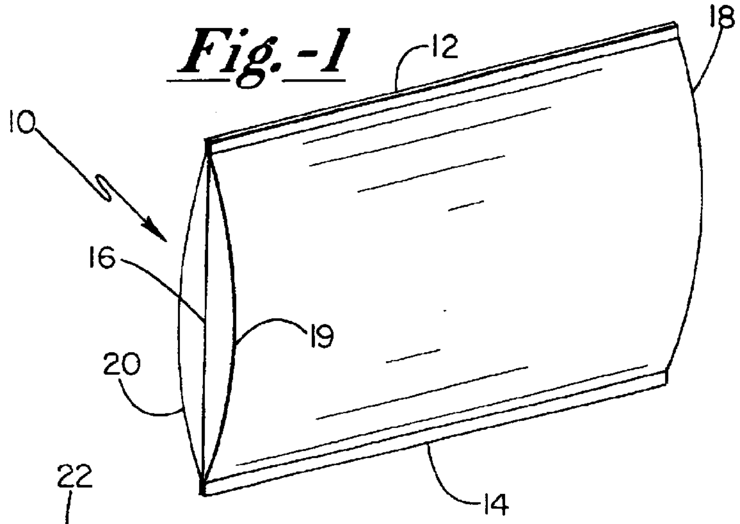
FIG. 1 is a perspective view showing the porous container of the present invention.

Referring now by characters of reference to the drawings, and first to FIG. 1, a porous container is shown. In the embodiment shown in FIG. 1, container 10 has a pouch-like appearance, with sealed side edges 12, 14, a closed end 16, and an initially open end 18. Porous container 10 is preferably fabricated from a porous material which is not susceptible to the various substances being inserted therein. In particularly preferred embodiments, container 10 is formed from fibrous paper that is permeable to a variety of fluids. Container 10 most preferably comprises DYNAPORE® long fiber papers manufactured by Schoeller & Hoesch GMBH. In particular, DYNAPORE® 26 gram heat sealed paper grade 123 is preferably utilized in the manufacture of container 10. Any material, however, that is fluid permeable and is not susceptible to the various substances being inserted into the container may be used.

In particular embodiments of the present invention, the porous material utilized in the manufacture of container 10 is biodegradable. The fibrous paper material described above, for example, contains about 90% by weight natural pulp fibers, and is therefore substantially biodegradable. Biodegradable products are highly sought after, particularly when used in natural environments, for their environmentally-friendly characteristics, both in manufacture and disposal. Thus, the biodegradable characteristic of the porous material utilized in the present invention is advantageous over conventional materials for the reasons set forth above.

Figure 2:
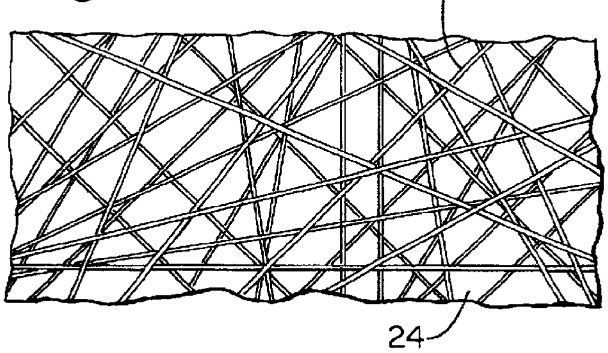
FIG. 2 is an enlarged cross-sectional view showing the fibrous nature of the porous material making up the porous container of the present invention.

The porous material utilized in the present invention is shown in detail in FIG. 2, where the intermeshing of the long fibers making up the material is illustrated. Such intermeshing of the long fibers provides the desired porosity, and therefore permeability of the present invention. As shown in FIG. 2, spaces between the long fibers designated at 22 form pores as designated at 24 therebetween. In preferred embodiments of the present invention, the pores 24 are sized and configured to allow microorganisms disposed within container 10 to pass therethrough at a rate of no more than about 0.5 g/day/$cm^2$ when the container is exposed to a stationary fluid environment. More preferably, the pores are sized and configured to allow the microorganisms to pass therethrough at a rate of no more than about 0.25 g/day/$cm^2$ when the container is exposed to a stationary fluid environment. Most preferably, the pores are sized and configured to allow the microorganisms to pass therethrough at a rate of no more than about 0.15 g/day/$cm^2$ when the container is exposed to a stationary fluid environment.

In preferred embodiments of the present invention, container 10 is formed by folding a sheet of desired material and desired size onto itself to form closed end 16. Side edges 12, 14 may then be sealed through a variety of sealing means, including heat sealing, ultrasonic sealing, or any other sealing technique which forms a stable seal at side edges 12, 14. Container 10 may also be formed from two distinct sheets of the desired material. Once container 10 is closed on three sides, the substance to be controllably released into the fluid environment is placed in the cavity of container 10 between closed end 16 and opposing sides 19, 20. Open end 18 is then sealed into a closed configuration as described above, thereby completely enclosing the contents within container 10. The configuration of container 10 described above is but one of a variety of configurations which may be used for container 10. The configuration for container 10 described herein is preferred only for its ease of manufacturing.

A particular advantage of the porous material descried herein for use in the present invention is its slow-release capability in a variety of fluid environments. Though the permeability values described above are in reference to stationary fluid environments, it is anticipated that similar results may be achieved in non-stationary fluid flow environments. In fact, the material disclosed herein was selected for its slow-release capability in high fluid flow environments, thereby allowing the present invention to be used in a variety of applications, including those applications in which controlled release is desired in a high fluid flow region.

A wide variety of substances may be utilized in the present invention for controlled release into fluid environments. Examples of such substances include pH-adjusting chemicals, salinity-adjusting chemicals, water-purification chemicals, minerals, and living organisms, such as various microorganisms including bacteria and enzymes. Any substances, however, may be utilized in the container of the present invention for controlled release into fluid environments, so long as the substances used are compatible with the porous material used in porous container 10.

In a particularly preferred embodiment, a blend of bacteria, nutrients, and a supporting fluid is inserted into container 10 for controlled release of the bacteria into fluid environments. In such an embodiment, container 10 forms a cultivation chamber for the bacteria, wherein new bacteria is generated by feeding on the nutrients while bacteria is also being controllably released into the surrounding fluid environment. Thus, a relatively compact and unitary container 10 may be used to both culture and controllably release bacteria into the surrounding fluid for treatment thereof. U.S. Pat. No. 5,879,932 further discusses the blend described herein and its uses.

The present invention also contemplates a variety of applications in which container 10 may be utilized. Container 10 may be disposable or may be reusable. In addition, container 10 may be used in combination with a variety of dispensers, which dispensers may allow container 10 to controllably release its contents in a floating orientation near the top surface of the fluid, in a suspending orientation controllably releasing its contents anywhere between the upper surface and the bottom level of the fluid, or in a sinking orientation where container 10 may controllably release its contents at or near the bottom level of the fluid.

Figure 3:
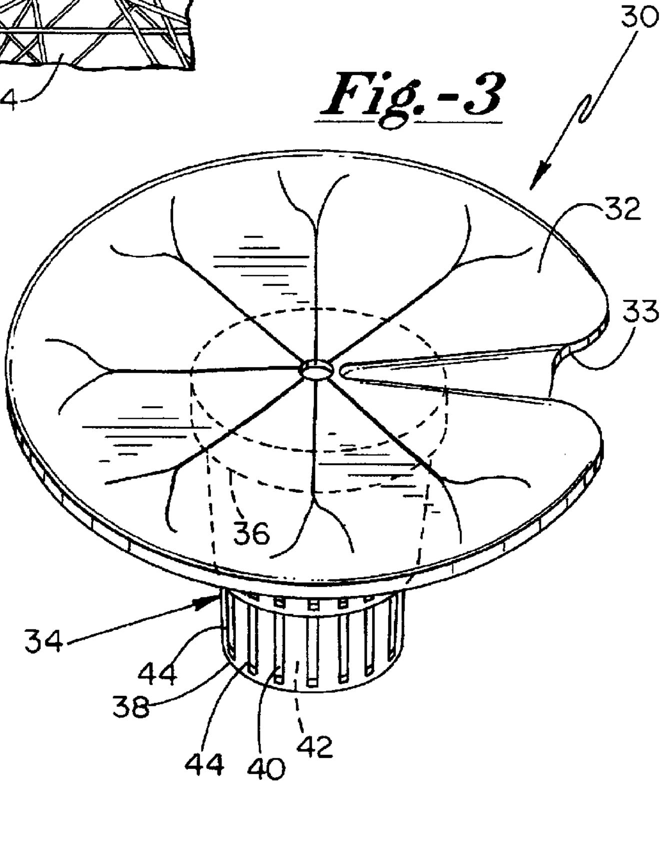
FIG. 3 is a perspective view of a dispensing system of the present invention.

A particular application contemplated by the present invention is illustrated in FIG. 3, where a dispensing vessel 30 is shown. Dispensing vessels 30 includes a relatively flat floating portion 32 and a growth chamber 34 depending downwardly therefrom. Preferably, growth chamber 34 is removably secured to a threaded flange 36 extending downwardly from a lower surface 33 of floating portion 32. Growth chamber 34 is preferably threadably secured and attached into threaded flange 36, though other removable securing means may also be used. Growth chamber 34 includes an exterior surface 38 and an interior surface 40, thereby defining a hollow chamber 42 therein. Growth chamber 34 further includes a plurality of open channels 44 extending from exterior surface 38 to interior surface 40, thereby providing hollow chamber 42 in fluid communication with the exterior of growth chamber 34. Preferably, container 10 is disposed in hollow chamber 42 for controlled release of its contents therein. The fluid communication through open channels 44 thereby provides distribution means for spreading the substances from within container 10 to fluid surrounding growth chamber 34.

In preferred embodiments, floating portion 32 and growth chamber 34 comprise polymeric materials, preferably polypropylene and/or polyethylene. Floating portion 32 and growth chamber 34 may be injection-molded, or molded through any other molding process. Floating portion 32 may also include a closed-cell foam. In highly preferred embodiments, such closed-cell foam comprises between about 1% and 5% by weight of floating portion 32. The composition of floating portion 32 provides sufficient buoyancy to cause dispenser 30 to float at or above the top surface of the fluid, even when container 10 is fully charged with its respective substances. The weight percentage of the closed-cell foam may be adjusted to provide varying degrees of buoyancy for use in applications requiring larger containers and/or heavier substances to be controllably released. Floating portion 32 may preferably be sized and configured to represent naturally-occurring objects to more aesthetically blend in with a natural environment. The embodiment shown in FIG. 3 is configured to represent a lily pad which may or may not include additional attachments thereto.

It is contemplated by the represent invention to utilize container 10 in conjunction with, or separately from, dispensing applications as described herein. An advantage of utilizing such dispensers with container 10 is the protection such dispensers provide for container 10 from intrusion or damage as a result of wildlife, or other intrusionary forces. Furthermore, such dispensers provide convenient means for placing container 10 in desired locations of the fluid environment to be treated.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A container for culturing and controllably releasing microorganisms contained therein into fluid environments, comprising:

a sealed pouch comprising a porous material and containing at least microorganisms and nutrients therein, said porous material having pores sized and configured to allow said microorganisms to pass through said pores at a rate of no more than about 0.5 g/day/$cm^2$ when said pouch is exposed to a stationary fluid environment, said pouch being adapted to allow said microorganisms to culture therewithin while developed microorganisms may be controllably released into said fluid environments.

2. A container as in claim 1 wherein said pores are sized and configured to allow said microorganisms to pass through said pores at a rate of no more than about 0.25 g/day/$cm^2$ when said pouch is exposed to a stationary fluid environment.

3. A container as in claim 1, wherein said pores are sized and configured to allow said microorganisms to pass through said pores at a rate of no more than about 0.15 g/day/$cm^2$ when said pouch is exposed to a stationary fluid environment.

4. A container as in claim 1, wherein said porous material is biodegradable.

5. A container as in claim 1, wherein said porous material is a fibrous paper material.

6. A system for controllably releasing substances into fluid environments, comprising:

a) a dispensing vessel; and b) a porous container disposed within said dispensing vessel and containing at least microorganisms and nutrients therewithin, said porous container comprising porous material having pores which are sized and configured to allow said substances to pass through said pores at a controlled rate of no more than about 0.5 g/day/$cm^2$ when said porous container is exposed to a stationary fluid environment, said porous container being adapted to allow said microorganisms to culture therewithin while developed microorganisms may be controllably released into said fluid environments.

7. A system as in claim 6, wherein said porous container is biodegradable.

8. A system as in claim 7, wherein said porous container comprises fibrous paper.

9. A system as in claim 6, wherein at least a portion of said dispensing vessel includes open channels extending through an exterior wall of said vessel, such that fluid surrounding said dispensing vessel may be in contact with said porous container disposed therein.

10. A system as in claim 6, wherein said dispensing vessel floats in an aqueous fluid environment.

11. A system as in claim 6, wherein said dispensing vessel includes a floating portion and a growth chamber removably secured thereto and depending downwardly therefrom, said growth chamber having an exterior surface and an interior surface thereby defining a hollow chamber, and a plurality of open channels extending from said exterior surface to said interior surface of said growth chamber, said porous container being disposed in said hollow chamber and in fluid communication with fluid surrounding said growth chamber via said open channels.

12. A system as in claim 11, wherein said floating portion includes a threaded flange extending downwardly therefrom, said flange being sized and configured to threadably receive said growth chamber.

13. A system as in claim 11, wherein said floating portion and said growth chamber comprise polymeric materials.

14. A system as in claim 6, wherein said dispensing vessel sinks in an aqueous fluid environment.

15. A method for culturing and controllably releasing microorganisms into fluid environments, comprising:

a) providing a porous container having microorganisms, nutrients, and a suspension fluid disposed therein, said porous container comprising material having pores which are sized and configured to allow said microorganisms to pass through said pores at a rate of no more than 0.5 g/day/$cm^2$ when said container is exposed to a stationary fluid environment; and b) placing said container in an aqueous environment, thereby allowing said microorganisms to culture within said container and controllably release into said aqueous environment.

16. A method as in claim 15, wherein said porous container is biodegradable.

* * * * *